United States Patent [19]
Brammann

[11] Patent Number: 5,468,150
[45] Date of Patent: Nov. 21, 1995

[54] MEANS FOR FASTENING ARTIFICIAL TEETH

[76] Inventor: Dierk Brammann, Bramfelder Strasse 103a, D-22305 Hamburg, Germany

[21] Appl. No.: 295,301

[22] Filed: Aug. 24, 1994

[30] Foreign Application Priority Data

Oct. 21, 1993 [DE] Germany .................. 9316043 U

[51] Int. Cl.⁶ .................................................. A61C 8/00
[52] U.S. Cl. ......................................... 433/173; 433/169
[58] Field of Search .............................. 433/172, 173, 433/174, 175, 176, 169, 177

[56] References Cited

U.S. PATENT DOCUMENTS

| | | | |
|---|---|---|---|
| 4,881,897 | 11/1989 | Franek et al. | 433/169 |
| 5,061,285 | 10/1991 | Koch | 433/173 X |
| 5,362,234 | 11/1994 | Salazar et al. | 433/169 |

FOREIGN PATENT DOCUMENTS

3300764A1  7/1984  Germany .
3615733A1  11/1987  Germany .
1463271A1  3/1989  U.S.S.R. .

*Primary Examiner*—Christopher A. Bennett
*Attorney, Agent, or Firm*—Faegre & Benson

[57] ABSTRACT

Means for fastening artificial teeth in the human jaw comprising an implant which is to be inserted into the jaw and is formed as a closed shell, a secondary portion including a connecting shank and being connectable to said implant, which secondary portion serves as a support for the artificial teeth, and a fastening element for fastening the artificial teeth to said secondary portion, with said connecting shank being held in the blind bore of said implant and at the proximal end comprising at least one slot parallel to the axis for providing a snap and spread connection with a rear cut in said blind bore, with said shank comprising a radially spreadable section which with the aid of a mandrel inserted into said secondary portion via an axial bore can be spread or, respectively, radially held in said implant, and said secondary portion comprising a radial shoulder which is supported by the distal end of said implant as soon as said spreadable section engages said rear cut.

17 Claims, 2 Drawing Sheets

5,468,150

MEANS FOR FASTENING ARTIFICIAL TEETH

FIELD OF THE INVENTION

The invention relates to a means for fastening artificial teeth in the human jaw.

BACKGROUND OF THE INVENTION

It has become known to fix sets of dentures, such as crowns, bridges or suchlike, in the jaw with the aid of so-called implants. An implant consisting of a material which harmonizes with the human body, such as titanium, is inserted into the jaw and is left there for some time to fasten. Usually, the implant is formed like a shell and at least distally comprises an inner bore for receiving a secondary portion which then serves as a support for the denture. It has become known to screw the secondary portion on the implant (primary portion) and to screw the denture on the secondary portion then.

From the German Offen. DE 33 00 764 an implant has become known, the implant body of which comprises a distal annular shoulder and a blind bore arranged coaxially with the annular shoulder and moving into engagement with a shank of said secondary portion. The top of the secondary portion is supported by the annular shoulder via a collar and a distance ring. The distance ring is defined as an elastically deformable annular lip. A blind bore results in a cavity provided deeply inside of the implant body. The pin carries a grip head engaging a cavity and comprising segments being elastically deformable against each other, as a result of which the head can be elastically compressed into at least the blind bore exit section and expands within the cavity so as to cause the grip head segments to engage the wall of the cavity in the upper and lower part. Thus, the secondary portion is supported in the implant partially axially and movably to the side.

SUMMARY OF THE INVENTION

The object of the invention is to provide a means for fastening artificial teeth in the human jaw so as to allow a precise shaping and fitting of these artificial teeth. Furthermore, a permanent position of the artificial teeth should be guaranteed.

Thus, the means for fastening artificial teeth comprises the following.

An implant primary portion is formed with a longitudinal blind bore closed at a distal end thereof. The implant primary portion is adapted and designed for insertion into the jaw.

A shell, formed with a longitudinal through bore, is adapted and designed for coaxial retention within the blind bore, so as to extend to less than the closed distal end of the blind bore.

An implant secondary portion having a longitudinal axis with a distally extending shank terminates in a distal enlargement and had a longitudinal through bore. The shank has a distal slot parallel to the longitudinal axis. The secondary portion also has a proximally enlarged head of larger cross-section than the blind bore. The shank is sized and adapted for being fully coaxially retained within the longitudinal through bore of the shell, so that the distal enlargement extends past a distal end of the shell.

A top is adapted and arranged to be matingly positioned on the enlarged head. The top is provided with a longitudinal through bore in coaxial alignment with the through bore of the secondary portion.

An elongated mandrel is sized and adapted to be longitudinally retained within the top through bore and within the through bole of the secondary portion for retaining the top in position against the enlarged head and for urging sections of the slotted shank radially outward.

According to the inventive means, the secondary portion is supported by the proximal end of the implant via a radial shoulder, thus providing a permanent position of the artificial teeth in axial direction. The counteracting forces in transverse direction and the direction of extraction are absorbed by the shank arranged within the shell of the implant. With the aid of the mandrel the shank in the end portion is radially expanded so as to cooperate with the rear cut and be safely kept in the shell of the implant. Thus, an insurmountable resistance is put up to an extraction force.

It is thinkable to form the rear cut by means of a cone-shaped area in the bore which is formed by a cone-shaped area at the outside of the expandable segments of the shank. According to an embodiment of the invention, however, this is to be preferred if the spreadable portion of the shank comprises an annularly surrounding outer surface which cooperates with an annularly surrounding opposite surface in the bore of the implant so as to cause the secondary portion to be axially drawn into the centre of the bore in case of a radial spread of the slotted portion of the secondary, portion. During insertion of the mandrel, for example by screwing it into the bore of the shank, the shank or, respectively, the secondary portion is axially pretensioned in the direction of the shell of the implant so that the secondary portion with its shoulder can tightly engage the shell of the implant. In this way, a defined gap between the secondary portion and the implant can be provided.

It is especially advantageous if the slotted or, respectively, spreadable section of the shank is spherical and with this spherical section engages a convex swelling in the bore of the implant. A continued spreading with the aid of the mandrel causes the shank to be drawn into the centre of the implant still further and thus forces the radial shoulder of the secondary portion against the outer end of the implant. The shank can be defined so as to fit into the blind bore of the implant approximately matingly with a relatively big portion for absorbing transverse forces. As a result of the described spherical shape of the free end of the shank, the area of engagement of the shank is in close proximity of the end of the blind bore so as to form a big lever arm for absorbing transverse forces.

In consequence of a corresponding shaping of the cross sections of the secondary portion or, respectively, the shank on the one hand and of a bore portion of the implant on the other hand, the secondary portion can be arranged in the implant so as to be secured against rotation.

It is known and usual to conically form the so-called top of the secondary portion, i.e. that section of the secondary portion which projects from the implant. According to and embodiment of the invention, a conical cap is provided which is matingly put on the free end of the secondary portion. Preferably, the free end comprises a cone which fittingly receives the conical cap. The use of a conical cap has the advantage that different caps with different outside dimensions and angles can be used which, depending on the application field, are put on the conical section of the secondary portion.

BRIEF DESCRIPTION OF THE DRAWINGS

The invention will be more detailedly explained hereinafter with the aid of drawings.

DETAILED DESCRIPTION OF THE INVENTION

Figure 1:
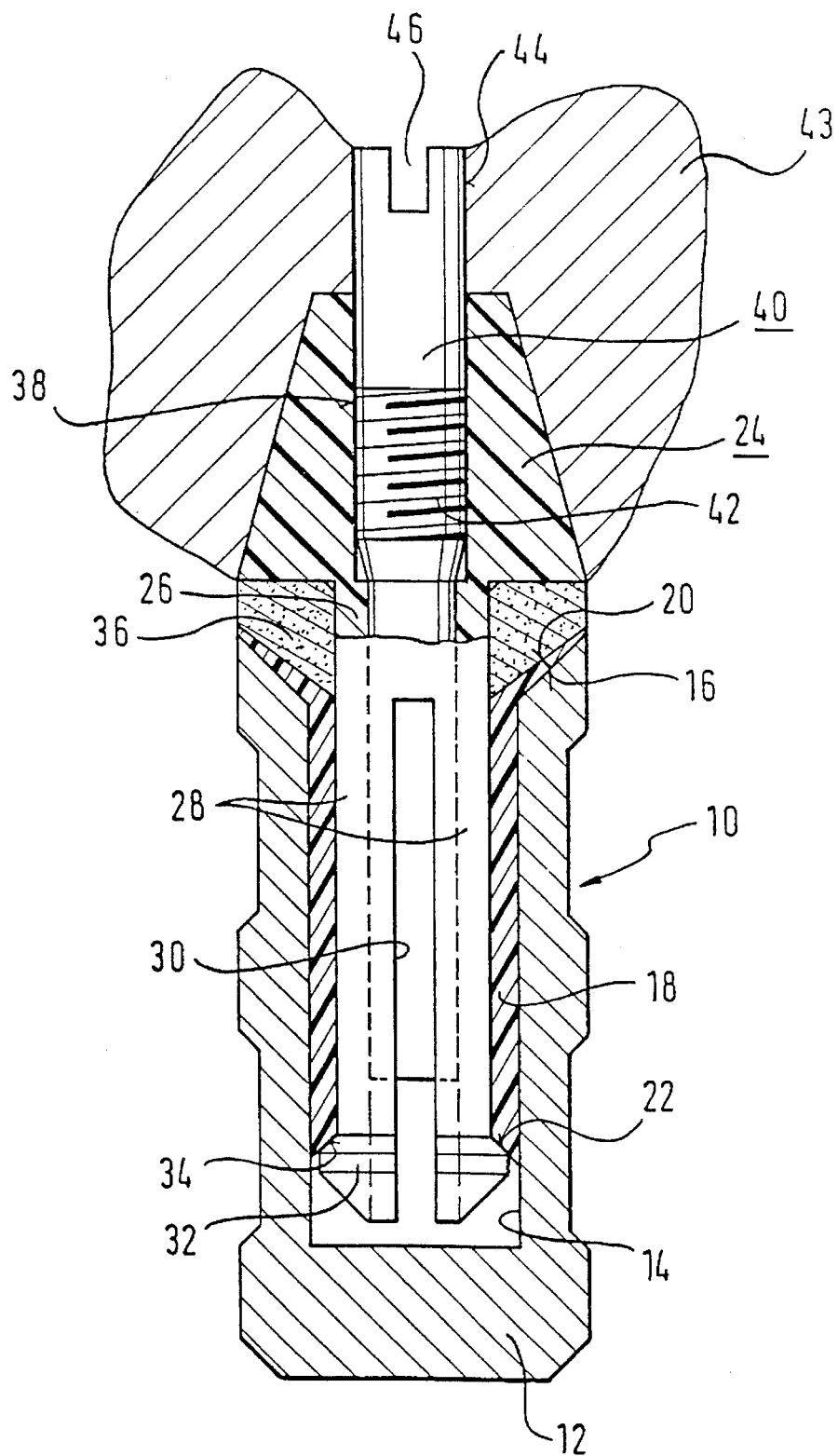
FIG. 1 shows a sectional view of a first embodiment of the means according to the invention.

FIG. 1 shows an implant 10 of a suitable material harmonizing with the human body, for instance titanium, which implant is formed like a shell and has a proximally closed end 12. The implant 10 comprises a cylindrical blind bore 14 and has been marginally resp. orally provided with a conical face 16. A cylindrical shell 18 has been inserted into the blind bore 14 and fastened thereto which cylindrical shell 18 may be composed of the same material as said implant 10 or of a suitable synthetic material, such as polymethylacrylate or a HPDE (high-density polyethylene). Also the shell 18 has been provided with a cone-shaped face 20 which is in alignment with the face 16. The shell 18 is shorter than the blind hole 14 so that a rear cut 22 results which is conically defined as well.

A cone-shaped secondary portion 24 comprises a shank 26 which, for instance, consists of four parallel legs 28 which are separated from each other by elongated slots 30 parallel to the axis. Each leg 28 at the lower end comprises a swelling 32 with an upper inclined surface 34 which cooperates with the correspondingly defined opposite surface 22 of the shell 18.

As can be seen, the shank 26 extends into the shell 18, with the thickened portions 32 extending within the area below the ends of shell 18. Besides, the shank 26 pushes through a proximally cone-shaped ring 36 of a suitable material harmonizing with the human body which material engages the annular-shaped lower side of the secondary portion 24 upwards. It may also be taken into consideration to form the ring 36 of a non-rigid material.

An elongated mandrel 40 extends through the through bore 38 of the secondary portion 24. The mandrel comprises a thread portion and cooperates with a thread portion 42 of the bore 38. A top 43 including a through bore 44 through which the mandrel 40 extends is fittingly arranged on the secondary portion 24, with said mandrel 40, however, being clearly projecting from the secondary portion 24. The mandrel 40 at its open end comprises a screw driver slot 46 so that it can be dislocated by means of a suitable tool.

To fix the implant in the jaw the secondary portion 24 together with the ring 36 put thereon, first of all, is inserted into the implant 10 so as to cause the swellings 32 to lock behind the face 22 of the shell 18. Thereafter, the top 43 is put on the secondary portion 24 and, then, the mandrel 40 is led through said top, the secondary portion 24, the ring 36 and the shell 18 and is screwed. As a result of the screw connection, a tensile strength can be realized between the secondary portion 24 and the implant 10 for safely fastening the secondary portion 24 and the implant 10, with the ring 36 being compressed. Thus, the denture 43 is tightly secured to the implant 10.

Figure 2:
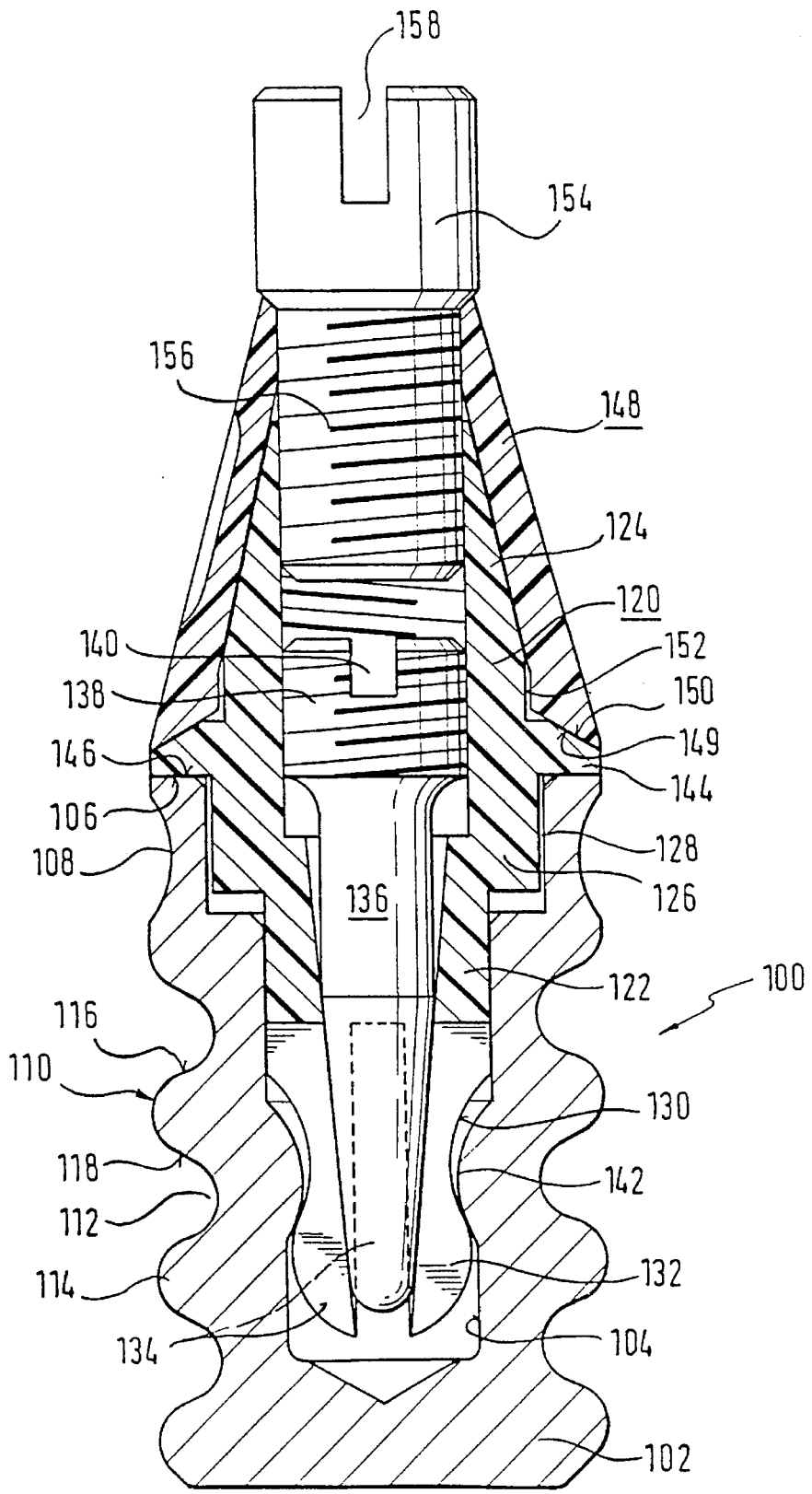
FIG. 2 shows a sectional view of a second embodiment of the means according to the invention.

According to the embodiment of FIG. 2, in turn, a shell-shaped implant 100 is shown which is closed at the proximal end 102. It comprises a blind bore 104 close to the upper end 106 which is formed as a plane annular area perpendicular to the axis of the implant 100. At the outside of the implant 100 an annular groove 108 is formed which in its cross-section is circular. Below said annular groove 108 a thread 110 is formed which comprises a threaded groove 112 being rounded in its cross-section as well as a rounded thread 114. The flanks 116 pointing upward are steeper than the opposite flanks 118 so that implant shell 100 is screwed into a preformed bore in the jaw in a relatively simple way but high extraction forces do result. The bore has a diameter which is identical to the core diameter of the thread 110. Thus, the implant can be inserted into the jaw without having to use any cement.

A secondary portion 120 comprises a shank 122 inserted into the blind bore 104 as well as a construction 124 outside the implant 100. As appears from FIG. 2, the shank 122 with a relatively big portion is matingly accommodated by bore 104 while a portion 126 of an enlarged diameter is received by an enlarged bore portion 128. The portion 126 in its cross-section is of a hexagonal shape. Accordingly, the recess 128 is hexagonal as well. Thus, the shank 122 is secured against rotation.

In the lower and proximal section the shank 122 comprises a circumferentially arranged groove 130 which is circular in its cross-section and forms a contraction. Below said contraction 130 a spherical portion 132 is provided which by means of slots 134 parallel to the axis is subdivided into four segments offset by 90°.

The secondary portion 120 comprises an axial through bore which in the upper area includes an inside thread. A mandrel 136 which in the lower area is cone-shaped comprises a head 138 including an external thread which can be screwed into said inside thread of the through bore. The head 138 comprises a screw driver slot 140 so as to screw the mandrel 136 into the secondary portion 120.

The blind bore 104 has a convex, circumferentially arranged swelling 142 pointing radially inward and forming a rear cut for the spherical section 132 of the shank 122. The secondary portion 120 comprises an annular flange 144 pointing radially outward and forming an annular area or shoulder 146 pointing downward. On the opposite side said flange comprises a cone-shaped area 149. When inserting the shank 122 into the blind bore 104 the segments of the spherical section 132 can escape inward by passing the swelling 142. Thereafter, they spread apart anti engage the bottom side of the swelling 142 as soon as the shoulder 146 engages the face 106 of the implant 100. The mandrel 138 spreads the segments of the spherical section 132 radially outward while being screwed in which causes the shank 122 to be axially held in the bore 104. The segments of the spherical section 132 and of the swelling 142 are defined so as to generate an axial force towards the end of the blind bore 104 at the moment the segments spread apart which causes the areas 106, 146 to be pressed against each other so as to form a defined gap. It should be remarked incidentally that the mandrel 136 needs not to be cone-shaped at all.

A cap 148 being cone-shaped inside and outside is put on the conical construction 124. The inner cone of the cap 148 mates with the outer cone of the construction 124. The lower end of the cap 148, as shown in FIG. 2 at 150, is cone-shaped, with the conical area being matingly cooperating with the conical area 148 of the annular flange 144. The construction 124 and the cap 148 in their cross-section are circular, in which case, however, as indicated at 152, at least one, preferably four positions offset by 90°, comprise flattenings at the outside of the construction 124 and the inside of the cap 148 for securing the cap 148 to the construction 124 so as to withstand any rotation.

As can be seen from FIG. 2, the cap 148 extends upward beyond the construction 124 and is secured to the secondary portion through the head 154 of a screw 156 which is screwed into the thread bore of the secondary portion 120. The screw 156 comprises a slot 158 for a screw driver. The length of the shank of the screw 156 is so dimensioned that it in any case is spaced apart from the head 138 of the mandrel 136 as soon as said mandrel has arrived at its final position.

The implant 100 consists of a suitable metal which harmonizes with the human body. The other parts consist of a suitable metal or synthetic material as it is also used for the means according to FIG. 1.

I claim:

1. An apparatus for fastening a dental implant in a jaw comprising:
    an implant primary portion formed with a longitudinal blind bore closed at a distal end thereof, the implant primary portion adapted and designed for insertion into the jaw;
    a shell formed with a longitudinal through bore adapted and designed for coaxial retention within the blind bore so as to extend to less than the closed distal end of the blind bore;
    a secondary portion having a longitudinal axis with a distally extending shank terminating in a distal enlargement and a longitudinal through bore, the shank having a distal slot parallel to the longitudinal axis, the secondary portion also having a proximally enlarged head of larger cross-section than the blind bore, the shank sized and adapted for being fully coaxially retained within the longitudinal through bore of the shell, so that the distal enlargement extends past a distal end of the shell;
    a top adapted and arranged to be matingly positioned on the enlarged head, the top provided with a longitudinal through bore in coaxial alignment with the through bore of the secondary portion; and
    an elongated mandrel sized and adapted to be longitudinally retained within the top through bore and within the through bore of the secondary portion for retaining the top in position against the enlarged head and for urging sections of the slotted shank radially outward.

2. The apparatus according to claim 1, wherein the mandrel includes an external thread which cooperates with an internal thread in the secondary portion.

3. The apparatus according to claim 1, wherein the top is an artificial tooth and the mandrel thus secures the artificial tooth to the secondary portion.

4. The apparatus according to claim 1, wherein the shank is formed with a plurality of slots and the shank is circumferentially formed with flattened faces which mate with flattened surfaces within the bore of the secondary portion so as to be secured against rotation with respect thereto.

5. The apparatus according to claim 1, wherein a proximal end of the bore of the implant primary portion comprises an enlarged diameter recess for matingly receiving an enlarged section of the secondary portion and wherein a circumference of the recess and of the enlarged section is non-circular.

6. The apparatus according to claim 1, wherein the proximally enlarged head of the secondary portion has a cone-shaped outer surface for receiving the top with a mating conical inner surface and with a conical outer surface.

7. The apparatus according to claim 6, wherein the top is adapted and arranged to be secured on the proximally enlarged head so as to be secured against rotation.

8. The apparatus according to claim 1, wherein the top matingly covers a radial flange of the proximally enlarged head, such that the flange forms a radial shoulder for confronting a proximal end of the implant primary portion.

9. An apparatus for fastening a dental implant in a jaw comprising:
    an implant primary portion formed with a longitudinal blind bore (104) closed at a distal end thereof, the bore provided with a radially constricting member at less than the distal end thereof, the implant primary portion adapted and designed for insertion into the jaw;
    a secondary portion having a longitudinal axis with a distally extending shank terminating in a distal enlargement and a longitudinal through bore, the shank having a distal slot parallel to the longitudinal axis, the secondary portion also having a proximally enlarged head of larger cross-section than the blind bore, the shank sized and adapted for being fully coaxially retained within the blind bore, so that the distal enlargement extends past the radially constricting member;
    a top adapted and arranged to be matingly positioned on the enlarged head, the top provided with a longitudinal through bore in coaxial alignment with the through bore of the secondary portion; and
    an elongated mandrel sized and adapted to be longitudinally retained within the top through bore and within the through bore of the secondary portion for urging sections of the slotted shank radially outward.

10. The apparatus according to claim 9, wherein the radially constricting member within the bore is formed by a separate hollow shell coaxially retained within the blind bore.

11. The apparatus according to claim 9, wherein the top is an artificial tooth and the mandrel includes an external thread which cooperates with an internal thread in the secondary portion to secure the artificial tooth to the secondary portion.

12. The apparatus according to claim 9, wherein the mandrel is sized and adapted to be fully retained within the secondary portion leaving sufficient space for a screw adapted to be inserted into the top for fastening the top to the secondary portion.

13. The apparatus according to claim 9, wherein the shank is formed with a plurality of slots and wherein the distal enlargement of the shank slotted section is a spherical portion spaced apart from a distal end of the shank by a radial contraction and the radially constricting member is a convex swelling pointing radially inward which engages the radial contraction.

14. The apparatus according to claim 9, wherein the shank is circumferentially formed with flattened faces which mate with flattened surfaces within the bore of the secondary portion so as to be secured against rotation with respect thereto.

15. The apparatus according to claim 9, wherein the secondary section of the secondary portion arranged outside the implant has a cone-shaped outer surface and a cap with a conical inner and outer surface is provided, with the inner surface being matingly arranged on the secondary section.

16. The apparatus according to claim 9, wherein the cap is arranged on the secondary section of the secondary portion so as to be secured against rotation.

17. The apparatus according to claim 9, wherein the cap engages and covers a radial flange of the secondary portion, with the flange forming the radial shoulder.

* * * * *